(12) United States Patent
Kuster et al.

(10) Patent No.: US 8,941,915 B2
(45) Date of Patent: Jan. 27, 2015

(54) ILLUMINATING DEVICE FOR AN OPERATING MICROSCOPE

(75) Inventors: Manfred Kuster, Widnau (CH); Heinz Suhner, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 816 days.

(21) Appl. No.: 13/053,268

(22) Filed: Mar. 22, 2011

(65) Prior Publication Data

US 2011/0279892 A1 Nov. 17, 2011

(30) Foreign Application Priority Data

Mar. 25, 2010 (DE) .......................... 10 2010 003 295

(51) Int. Cl.
 *G02B 21/22* (2006.01)
 *G02B 21/00* (2006.01)
 *A61B 19/00* (2006.01)
 *G02B 27/14* (2006.01)

(52) U.S. Cl.
 CPC ........ *G02B 21/0012* (2013.01); *A61B 19/5223* (2013.01); *G02B 21/22* (2013.01); *A61B 19/5202* (2013.01); *G02B 27/144* (2013.01)
 USPC ....................................................... 359/376

(58) Field of Classification Search
 USPC ................. 359/243, 368–390, 838–839, 850; 351/221, 243
 See application file for complete search history.

(56) References Cited

U.S. PATENT DOCUMENTS

| 5,126,877 | A | 6/1992 | Biber | |
| 6,011,647 | A | 1/2000 | Geschwentner | |
| 6,624,932 | B2 * | 9/2003 | Koetke | 359/389 |
| 6,975,451 | B2 | 12/2005 | Sander | |
| 7,142,359 | B2 * | 11/2006 | Sander | 359/385 |
| 7,206,127 | B2 * | 4/2007 | Sander | 359/376 |

* cited by examiner

*Primary Examiner* — Suchin Parihar
*Assistant Examiner* — Tamara Y Washington
(74) *Attorney, Agent, or Firm* — Hodgson Russ LLP

(57) ABSTRACT

The present invention relates to an illuminating device for an operating microscope including two observation beam paths for a first observer and two observation beam paths for a second observer. An illuminating system provides two parallel illuminating beam paths and a deflecting device, for deflecting the parallel illuminating beam paths onto an object that is to be observed. The deflecting device includes a first semitransparent deflector element which is associated with a first observation beam path of the first observer and a first observation beam path of the second observer, and a second semitransparent deflector element, which is associated with a second observation beam path of the first observer and a second observation beam path of the second observer. The first illuminating beam path acts exclusively on the first deflector element and the second illuminating beam path acts exclusively on the second deflector element.

15 Claims, 3 Drawing Sheets

ILLUMINATING DEVICE FOR AN OPERATING MICROSCOPE

CROSS REFERENCE TO RELATED APPLICATIONS

Figure 1:
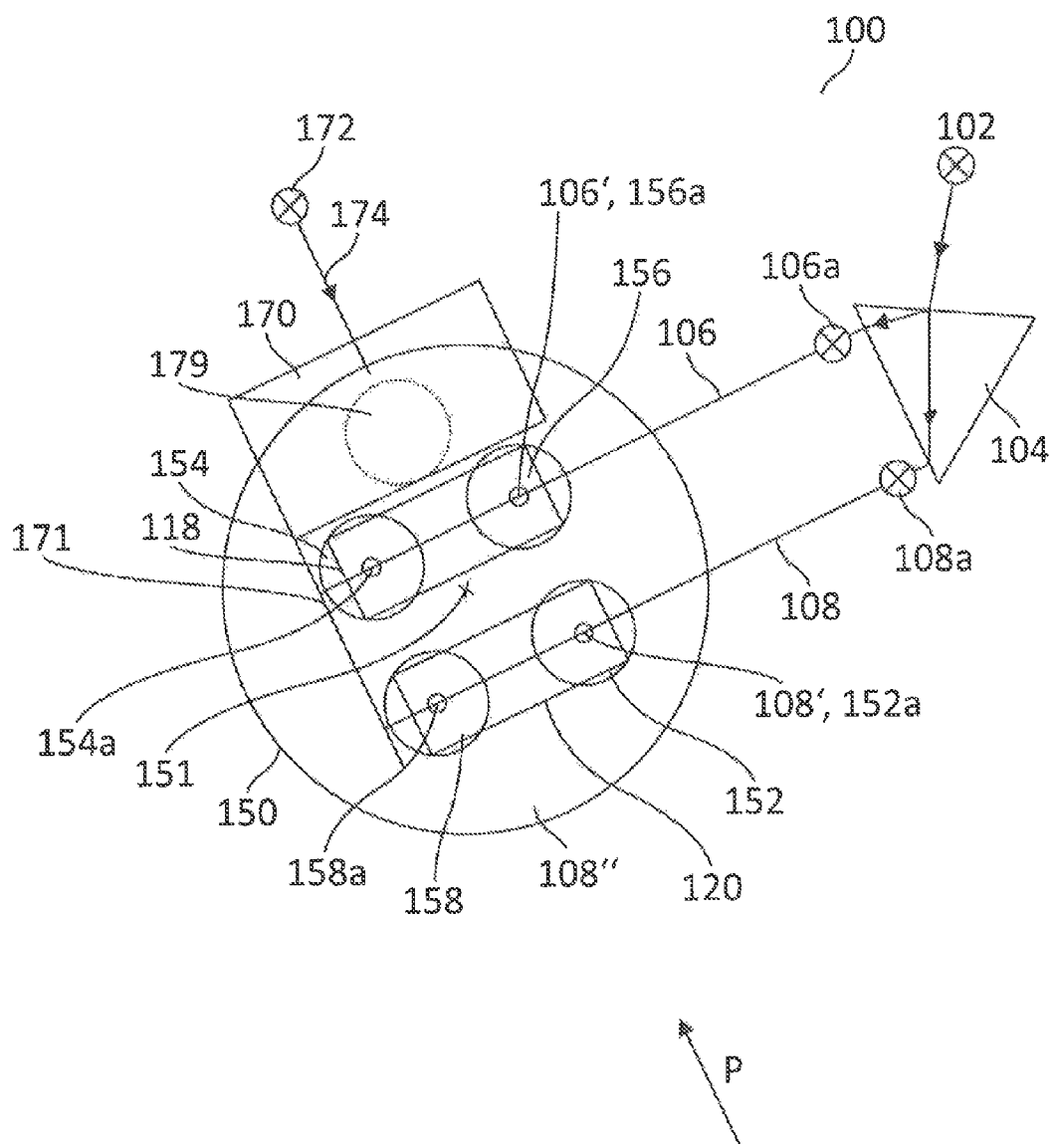

This application claims priority of the German patent application 10 2010 003 295.6 filed Mar. 25, 2010, the entire disclosure of which is incorporated by reference herein.

FIELD OF THE INVENTION

The present invention relates to an illuminating device for an operating microscope of a type having two observation beam paths for a first observer (main surgeon) and two observation beam paths for a second observer (assistant), and to a stereomicroscope of a type having a main objective and a magnification system downstream from the main objective.

BACKGROUND OF THE INVENTION

Illuminating devices for operating microscopes generally use an illuminating beam path which is at an angle in the region of about 6° to the observation beam path (so-called 6° illumination). This avoids the undesirable shadowing which would occur at larger angles between the observation beam path and the illuminating beam path.

Eye surgery places additional special demands on the illumination of a microscope. To start with, a sufficiently plastic image is obtained at an illuminating angle of, again, about 6°. However, for certain ophthalmic observations or interventions it is necessary to produce the so-called red reflex. In this, the pupil of the eye being operated on shines reddish as a result of the light refracted by the retina. This method of illumination is of great importance in cataract operations, for example, as tissue residues show up particularly well in the counter-light of the red reflex. The production of the red reflex requires smaller angles between the observation beam path and the illuminating beam path, the angles preferably being in the range from 0° to 2° (so-called 0° or 2° illumination).

Operating microscopes which are configured with two pairs of stereoscopic observation beam paths for a first observer (main surgeon) and a second observer (assistant), respectively, often have the disadvantage that the red reflex is very easy for the main surgeon to see but cannot be seen satisfactorily by the co-observer. The latter will only see a good red reflex in one of his two observation channels, depending on his position, either to the right or left of the main surgeon. This has an adverse effect on stereoscopic viewing.

DE 040 28 605 discloses an illuminating device for an operating microscope with an illuminating system that is arranged outside the optical axis of the microscope objective and illuminates the operating area parallel to the axis of the objective through the microscope objective, and a deflector element on the side of the microscope objective remote from the object, which illuminates the operating area with a fraction of the illuminating light along the axis of the objective. This illuminating device is characterised in that the illuminating system is equipped, on the objective side, with a reflecting element which reflects the illuminating light parallel to the objective axis towards the microscope objective, and in that the deflector element illuminates the operating area at an angle of inclination relative to the objective axis that is smaller than the angle of inclination at which the reflecting element illuminates the operating area. The larger angle of inclination is preferably 6°, the smaller angle is variable from 0° to 6°. The illuminating device described in this publication does not contain any solution for providing, for example, a red reflex for a second observer (assistant).

DE 103 11 000 B4 discloses an illuminating device for a microscope having at least one observation beam path, particularly an operating microscope, with an illuminating system and a deflector device for deflecting light emanating from a light source onto an object that is to be observed, e.g. an eye that is to be operated on, the deflector device providing illumination of the object at different illuminating angles with respect to the at least one observation beam, and the deflector device comprising two deflector elements that are at least partly configured as physical beam splitters. This illuminating device uses three deflector elements to provide a 6° and a 2° illumination for a main surgeon and an assistant.

An illuminating device is known from DE 102 08 594 in which, in one embodiment, two parallel illuminating beam pencils are used. These are deflected from deflector elements with a total mirror finish. Because of the total mirror finish these deflector elements cannot be placed in the observation beam paths, which means that certain minimum angles between the optical axis of a main objective or the observation beam paths and the illuminating beam paths are unavoidable. However, to provide the optimum red reflex, the angles should be as small as possible.

SUMMARY OF THE INVENTION

The present invention seeks to provide an illuminating device for an operating microscope that is as simple as possible, of compact design and cheap to produce, and which provides both a first observer (main operator) and a second observer (assistant) with an optimised red reflex at the same time. This aim is achieved with an illuminating device having two semitransparent deflector elements, a first of which is associated with a first observation beam path of the first observer and a first observation beam path of the second observer, and a second of which is associated with the second observation beam path of the first observer and the second observation beam path of the second observer. In corresponding manner, a compact stereomicroscope, particularly an operating microscope, can be provided by means of the invention.

As a result of the inventive feature of providing two semitransparent deflector elements, a first of which is associated with a first observation beam path of the first observer and a first observation beam path of the second observer, and a second of which is associated with the second observation beam path of the first observer and the second observation beam path of the second observer, first of all the number of deflector elements required can be minimised. By the term "associated" is meant, in particular, that the respective deflector elements overlap the observation beam paths assigned to them at least partly and more particularly completely, i.e. the observation beam paths intersect with the deflector elements with part of their pencil cross-section. Moreover, the fact that each of the two illuminating beam paths is made available partly to the first observer and partly to the second observer ensures that the red reflex is of substantially the same quality for both observers. Furthermore, thanks to their semitransparency, the deflector elements used according to the invention can be positioned anywhere in the observation beam paths, without any adverse effects for the observers. In particular, this measure provides zero degree illumination, with which an optimum red reflex is obtained.

The further feature according to the invention that the first illuminating beam path acts exclusively on the first deflector element, and the second illuminating beam path acts exclusively on the second deflector element, i.e. each of the parallel illuminating beam paths acts on only one deflector element, ensures that undesirable light reflexes and/or reflections are substantially avoided within the microscope. In particular, crosstalk between individual channels of the operating microscope can be effectively prevented.

In all, as will require no further explanation, the two observation beam paths of the main surgeon are used for stereoscopic viewing by the main surgeon, and the two observation beam paths of the assistant are used for stereoscopic viewing by the assistant.

The orientation of the illuminating beam paths relative to the deflector elements can also be described in terms of the stereo base of the main surgeon or assistant. The (parallel) observation beam paths of the main surgeon define the stereo base of the main surgeon by their spacing from one another. Analogously, the (parallel) observation beam paths of the assistant define the stereo base of the assistant. As already mentioned, the deflector elements each serve to illuminate one observation beam path of the main surgeon and one observation beam path of the assistant.

A line passing through these two observation beam paths represents the longitudinal axis of the respective deflector element. The present invention is characterised in that the stereo bases of the main surgeon and assistant run diagonally with respect to these longitudinal axes of the deflector elements, particularly at an angle of 30°-60°, preferably 45°.

This deviation from conventional illuminating beam path allocations makes it possible according to the present invention to operate two observation beam paths of a main surgeon and two observation beam paths of an assistant with only two deflector elements. This results in particular in an optimum red reflex for both the main surgeon and the assistant. Moreover, an illuminating device that requires only two deflector elements for the stated purpose is very compact in its construction. It has also proved advantageous that the illuminating beam paths striking the deflector elements can be shone in diagonally with respect to the imaginary lines joining the two observation beam paths of the main surgeon and of the assistant, respectively.

Advantageous embodiments of the invention are the subject of the dependent claims.

According to a preferred embodiment of the illuminating device according to the invention, the illuminating system used, by means of which the deflector elements are acted upon with light, has a single light source. A light source of this kind may cooperate with a beam splitter element such as a Köster prism such that two suitable parallel illuminating beam paths can be produced. Alternatively, bundles of fibres proceeding from the light source may be used to provide the respective illuminating beam paths. Two or more independent light sources may also be used.

It is preferable if the two deflector elements used according to the invention serve to provide 0° to 2° illumination for the first and second observer.

Expediently, the illuminating device according to the invention comprises at least one additional deflector element for providing further illumination at a greater angle, particularly illumination of the surrounding area (peripheral illumination) or 6° illumination. Because of the compactness of the 0° or 2° illumination which requires only two deflector elements according to the invention, further deflector elements for the 6° illumination can be arranged particularly easily and flexibly. An additional deflector element of this kind may be acted upon by an illuminating beam path which runs substantially parallel to the first and second illuminating beam paths, while in this case the additional deflector element has substantially the same spatial orientation as the first and second deflector elements. It is also possible to configure an additional illuminating beam path at an angle, for example substantially perpendicular, to the first and second illuminating beam paths, the additional deflector element in this case having a correspondingly different spatial orientation.

The first deflector element and the second deflector element are conveniently at substantially the same spacing from a main objective, onto which they deflect the light received from the illuminating system. This embodiment is very compact in construction, particularly in the vertical or perpendicular direction.

In a preferred embodiment, it is also possible to arrange the third deflector element at the same height as the first and second deflector elements. By this means it is also possible to produce an illuminating system that provides 0° or 2° illumination and 6° illumination in a very compact manner.

The additional deflector element may also be configured as a semitransparent (partly transparent) reflecting element and/or as an at least partly fully mirrored reflecting element. When a semitransparent reflecting element is used it is possible in particular to illuminate another beam path, for example for documentation (as a third observation option in addition to the main surgeon and assistant), while supplying a red reflex. The use of a fully mirrored reflecting element allows particularly effective illumination.

According to another preferred embodiment of the illuminating device according to the invention, the first and/or second deflector element is fully mirrored at least in parts. By this means, areas of the deflector elements located outside the projection of the observation beam paths, for example, can be configured to be fully mirrored without affecting the observation beam paths. It is also possible for example to construct small areas of the deflector elements that are located within the projection of the observation beam paths or are acted upon by them with a full mirror finish. As a result the red reflex can be positively influenced, for example, without the observer noticing the fully mirrored areas within the observation beam paths.

Expediently, the illuminating device according to the invention comprises a device for reducing unwanted light reflexes and/or reflections within the operation microscope. Using a device of this kind, in particular, crosstalk between individual channels of the operating microscope can be further minimised. Reference should be made at this point to the use of light traps, in particular.

According to another preferred embodiment, the first and the second deflector elements are formed in a unified glass block. Mounting them in a glass block in this way serves to reduce unwanted reflexes or reflections, as glass-air surfaces which may produce unwanted reflections of this kind are minimised.

It is also advantageously possible to construct the first deflector element and the second deflector element by means of a semitransparent reflecting element. This semitransparent reflecting element may have opaque regions to distinguish the illuminating beam paths from one another. It may also have fully mirrored regions, particularly outside the observation beam paths that run through it. The red reflex can be further optimised by these fully mirrored areas, as already mentioned.

Further advantages will become apparent from the description of the attached drawings.

It will be understood that the features mentioned above and those still to be explained hereinafter may be used not only in the particular combination stated but also in other combinations or on their own without departing from the scope of the present invention.

BRIEF DESCRIPTION OF THE DRAWING VIEWS

The invention will now be explained further by a description of preferred embodiments with reference to the attached drawings.

In the drawings

Figure 2:
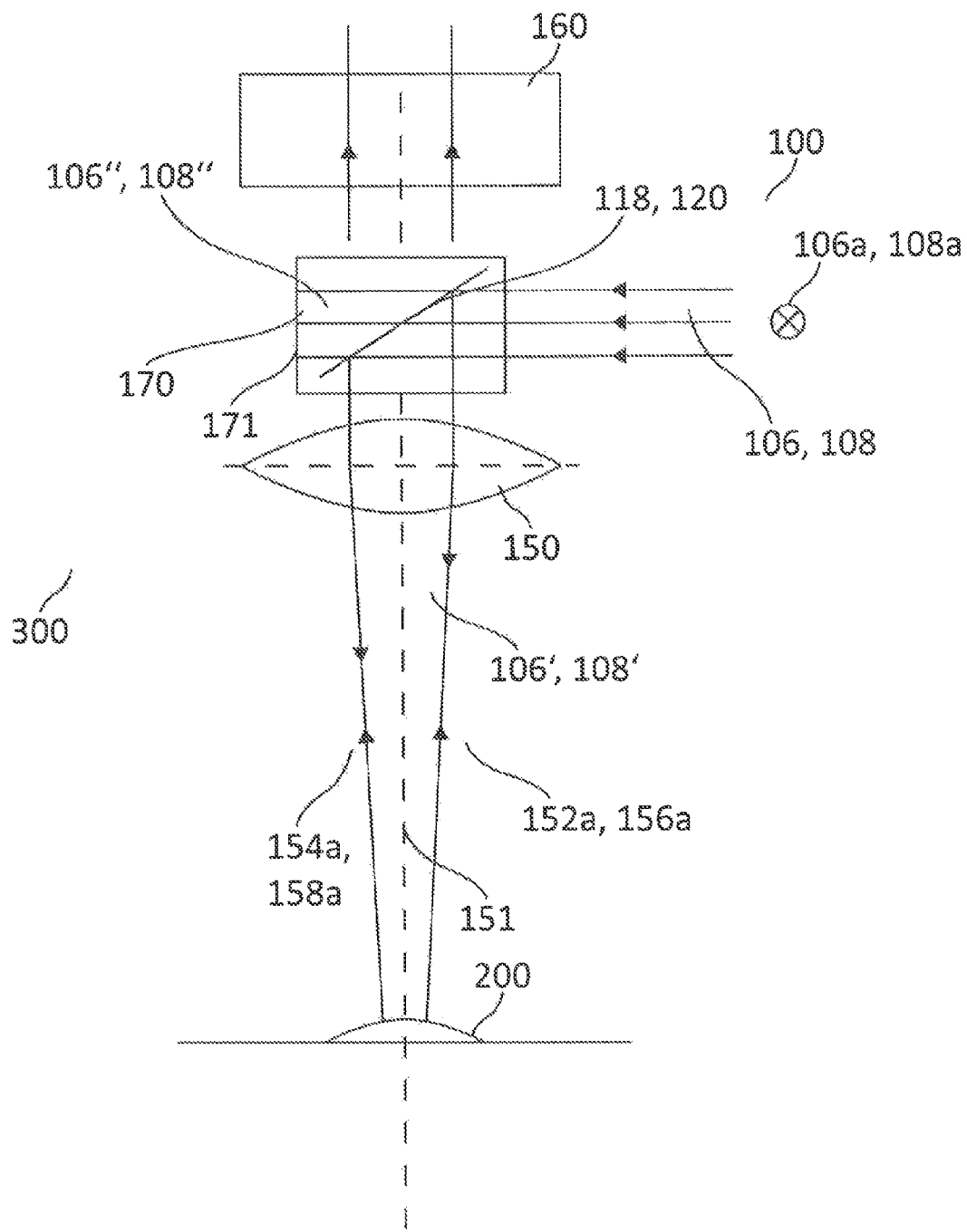
Figure 3:
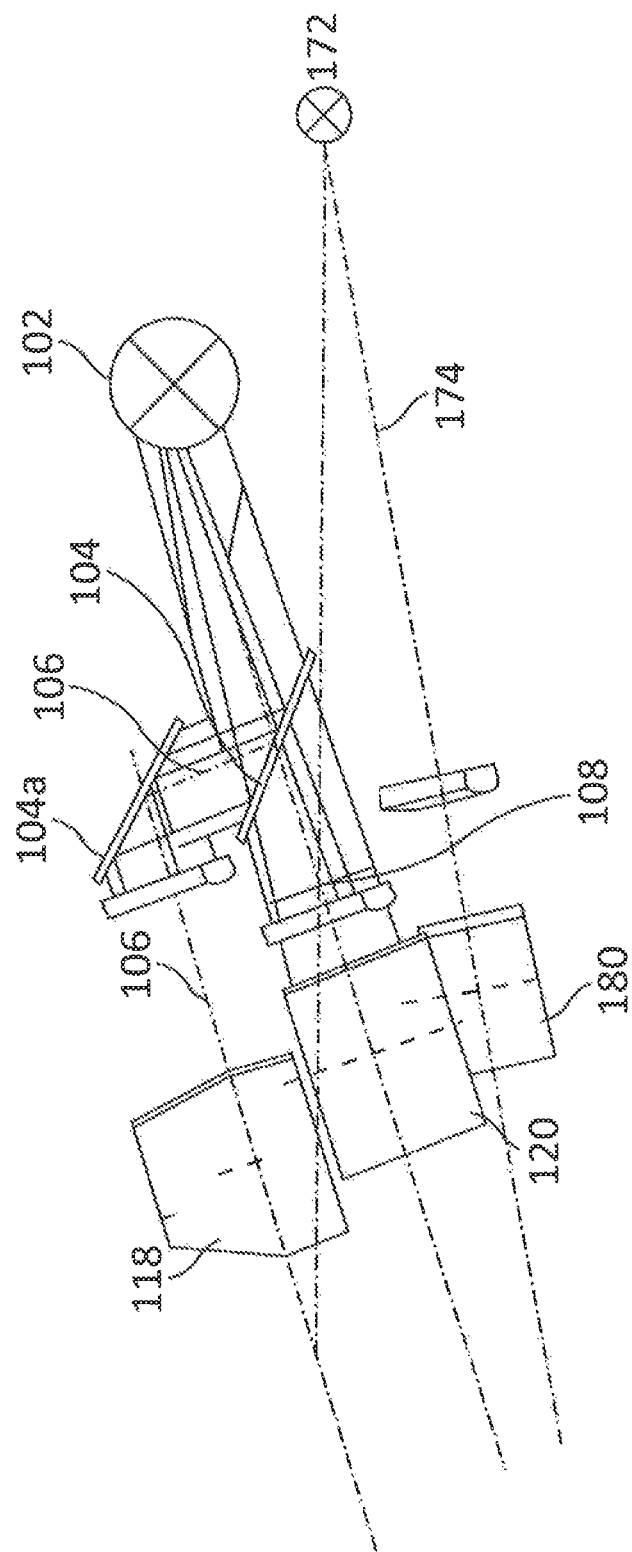

FIG. 1 is a plan view of a first preferred embodiment of an illuminating device according to the invention, FIG. 2 is a schematic side view of the illuminating device in the direction of the arrow P according to FIG. 1, and FIG. 3 is a plan view of another preferred embodiment of an illuminating device according to the invention.

DETAILED DESCRIPTION OF THE INVENTION

In FIGS. 1 and 2, a preferred embodiment of the illuminating device according to the invention, comprising a main objective 150 and, downstream thereof, a magnification system (including the requisite tubes and eyepieces) 160 of a microscope 300, is generally designated 100.

The microscope 300 is an operating stereomicroscope which provides two observation beam paths 152, 154 for a main surgeon and two further observation beam paths 156, 158 for an assistant. The observation beam paths running in corresponding observation channels are represented in FIG. 1 as circles and in FIG. 2 by means of the observation axes 152a, 154a, 156a, 158a associated therewith. There is no need to go into detail about specific items of equipment (such as e.g. lenses and zoom systems) for providing four such observation channels within the scope of the present invention relating to an illuminating device.

The illuminating device 100 according to the invention first of all has a light source 102. Two parallel illuminating beam paths 106, 108 are generated by means of a beam splitter 104 (diagrammatically shown in FIG. 1), which may be configured as a Köster prism, for example. As will be self-explanatory, these illuminating beam paths 106, 108 may be regarded as light beams emanating from (virtual) light sources 106a, 108a. It is also possible to provide two (actual) light sources 106a, 108a instead of the light source 102 and beam splitter 104. The use of fibre illuminating devices is also possible.

The illuminating device 100 also comprises two deflector elements 118, 120 as a deflector device.

The first deflector element 118, which the illuminating beam path 106 strikes first, is configured as a semitransparent element (physical beam splitter), particularly a semitransparent mirror. The second deflector element 120 that the illuminating beam path 108 strikes is of corresponding construction, for example again in the form of a semitransparent mirror. It is possible to construct areas of the deflector elements 118, 120, for example regions located outside or in the edge region of the observation beam paths, with a full mirror finish. It is also possible for example to construct small areas of the deflector elements in the centre of the observation beam paths, i.e. substantially within the region of the observation axes, with a full mirror finish. This measure allows the red reflex to be influenced, for example.

The deflector elements 118, 120 or their longitudinal axes which can be defined as the connecting lines between the observation axes of their associated observation beam paths, are oriented diagonally or at an angle of 45° to the main surgeon's stereo base (imaginary connecting line between the observation axes 152a, 154a of the main surgeon) or the assistant's stereo base (imaginary connecting line between the observation axes 156a, 158a of the assistant). The deflector elements are arranged in the immediate vicinity of the optical axis 151 of the main objective 150 and thus close to the observation axes 152a, 154a, 156a, 158a, and therefore provide a 0° or 2° illumination of the object 200 for each observation beam path.

The illuminating device also comprises another deflector element 170 which is acted upon by another light source 172. The deflector element 170 is arranged at a greater distance from the optical axis 151 of the main objective 150 and serves to provide a 6° illumination for the observation beam paths 152, 154, 156, 158, which is advantageous for increasing the contrast for users of the microscope. For operating techniques in which the red reflex is not required, it may be sufficient to use only the 6° illumination. The deflector element 170 is preferably configured as a fully mirrored reflector, and also arranged at an angle of 45° to the preferably horizontally extending additional illuminating beam path 174. It is possible to combine the light sources 102, 172 to form a single light source, and to produce the illuminating beam paths 106, 108, 174 by means of suitable beam splitter devices and/or light conducting systems (fibre optics).

It is also possible to make the deflector element 170 semitransparent, so that an additional observation beam path 179 (shown by dashed lines) can be illuminated. A documentation device, for example, may be connected to this observation beam path 179. For the observation beam path 179, a 0° to 2° illumination is thus provided, for example, rendering the red reflex visible even within the scope of the documentation, as no light whatsoever has to be coupled out of the observation beam paths for the documentation.

The core of the invention lies in the particular arrangement of the deflector elements 118, 120 relative to the observation beam paths 152, 154 of the main surgeon and 156, 158 of the assistant:

As can be seen from the Figures, the first deflector element 118 is associated with the first observation beam path 154 of the main surgeon, and the first observation beam path 156 of the assistant. This means that the horizontal projection of the deflector element 118, as shown in FIG. 1, at least partially overlaps the first observation beam path 154 of the main surgeon and the first observation beam path 156 of the assistant. This overlap can be selected as desired, while in particular a total overlap is also possible. The illuminating beam path 106 is partly deflected through 90° by the first deflector element 118 in the direction of the main objective 150 (partial beam paths 106'), and partly transmitted without any deflection (partial beam path 106").

The partial beam path 108 strikes the second deflector element 120 analogously, this second deflector element being associated with the second observation beam path 152 of the main surgeon and the second observation beam path 158 of the assistant. The second deflector element 120 is also of semitransparent construction. The partial beam path deflected through 90° in the direction of the main objective is designated 108', and the transmitted partial beam path is designated 108".

The transmitted partial beam paths 106", 108" expediently strike a light trap 171 (not shown in detail) to minimise unwanted reflections.

The illuminating system shown thus provides both the main surgeon and the assistant with an optimum red reflex, and achieves this with only two deflector elements 118, 120 and preferably only one light source 102.

According to the embodiment shown in FIGS. 1 and 2, the two deflector elements 118, 120 are arranged at the same height relative to the optical axis 151. The same is true of the additional deflector element 170. This measure advantageously makes it possible to minimise the overall height of an operating microscope equipped with the illuminating device according to the invention. It is also possible to mount the deflector elements 118, 120 in an offset position relative to the optical axis 151, i.e. at different heights. Two deflector elements thus offset from one another in the vertical direction can also be acted upon by only a single light source using a corresponding beam splitter.

The deflector elements 118, 120 may be provided in a coherent glass block (not shown). In this way the number of glass-air surfaces can be reduced, thus further reducing unwanted reflections. The deflector elements 118, 120 may also be constructed as a single reflecting element, while opaque regions may be provided between the deflector elements 118, 120 which are of semitransparent construction according to the invention. These opaque regions may be configured to be fully absorbent or fully mirrored. Using these measures, the illuminating beams striking the object that is to be observed can be delimited from one another or shaped in any desired manner. It is possible for example to provide illuminating beam paths of rectangular, square or round cross-section.

Cross-sections of illuminating beam paths of this kind may also be obtained by a suitable choice of the lighting medium of the light source, with particular reference to halogen lamps, LEDs, etc.

FIG. 3 is a plan view of a particularly preferred embodiment of the illuminating device according to the invention viewed in schematic plan view. The same or similar components have been given the same reference numerals here. Beam paths emanating from a light source 102 are split by a beam splitter element 104 into illuminating beam paths 106, 108. The element 104 is embodied here as a semitransparent mirror. The illuminating beam path 106 is deflected again from another, fully mirrored element 104a, so that the illuminating beam paths 106, 108 then run parallel to one another again. The illuminating beam path 106 strikes the first semitransparent deflector element 118, the illuminating beam path 108 strikes the second semitransparent deflector element 120. The respective observation beam paths which are substantially overlapped by these deflector elements 118, 120 are not shown here.

Another light source for providing illumination of the surrounding area is designated 172. This acts on an additional deflector element 180, which may be semitransparent or fully mirrored, with another illuminating beam path 174. The embodiment shown in FIG. 3 is characterised in that both the illuminating beam paths 106, 108 needed for the red reflex illumination and the illuminating beam path 174 used for illuminating the surrounding area are irradiated from substantially the same direction, i.e. substantially parallel to one another. This results in a particularly compact construction.

What is claimed is:

1. An illuminating device for an operating microscope, the operating microscope having a main objective, two observation beam paths for a first observer and two observation beam paths for a second observer, the illuminating device comprising:
    an illuminating system for providing two parallel illuminating beam paths; and
    a deflecting device arranged to deflect the parallel illuminating beam paths onto an object to be observed by the microscope;
    wherein the deflecting device includes a first semitransparent deflector element associated with a first observation beam path for the first observer and a first observation beam path for the second observer, and a second semitransparent deflector element associated with a second observation beam path for the first observer and a second observation beam path for the second observer, the first illuminating beam path acting exclusively on the first semitransparent deflector element and the second illuminating beam path acting exclusively on the second semitransparent deflector element.

2. The illuminating device according to claim 1, wherein the illuminating system comprises only one light source.

3. The illuminating device according to claim 1, wherein the first and second semitransparent deflector elements are arranged to illuminate the object at a first illuminating angle relative to the observation beam paths for 0° to 2° illumination for the first and second observers.

4. The illuminating device according to claim 3, further comprising an additional deflector element arranged to illuminate the object at a second illuminating angle greater than the first illuminating angle greater relative to the observation beam paths.

5. The illuminating device according to claim 4, wherein the additional deflector element provides illumination of an area surrounding the object or 6° illumination of the object.

6. The illuminating device according to claim 1, wherein the first semitransparent deflector element and the second semitransparent deflector element are at the same distance from the main objective of the microscope.

7. The illuminating device according to claim 4, wherein the additional deflector element is arranged at the same height as the first and second semitransparent deflector elements.

8. The illuminating device according to claim 1, wherein the first and second semitransparent deflector elements are semitransparent mirror elements.

9. The illuminating device according to claim 4, wherein the additional deflector element is a semitransparent mirror element.

10. The illuminating device according to claim 4, wherein the additional deflector element has a portion that is fully mirrored.

11. The illuminating device according to claim 10, wherein the additional deflector element provides an additional observation channel, whereby a documentation device may be connected to the microscope.

12. The illuminating device according to claim 1, wherein at least one of the first and second semitransparent deflector elements has a portion that is fully mirrored.

13. The illuminating device according to claim 1, further comprising a light trap arranged to prevent unwanted reflections within the microscope.

14. The illuminating device according to claim 1, wherein the first and second semitransparent deflector elements are formed in a unified glass block.

15. A stereomicroscope comprising:
    a main objective;
    a magnification system downstream from the main objective;
    two observation beam paths for a first observer and two observation beam paths for a second observer;
    an illuminating system for providing two parallel illuminating beam paths; and
    a deflecting device arranged to deflect the parallel illuminating beam paths onto an object to be observed by the stereomicroscope;

wherein the deflecting device includes a first semitransparent deflector element associated with a first observation beam path for the first observer and a first observation beam path for the second observer, and a second semitransparent deflector element associated with a second observation beam path for the first observer and a second observation beam path for the second observer, the first illuminating beam path acting exclusively on the first semitransparent deflector element and the second illuminating beam path acting exclusively on the second semitransparent deflector element.

* * * * *